(12) United States Patent
Eddolls et al.

(10) Patent No.: US 8,143,406 B2
(45) Date of Patent: Mar. 27, 2012

(54) PROCESS FOR THE MANUFACTURE OF HI-6 DIMETHANESULFONATE

(75) Inventors: Jonathan Eddolls, Liverpool (GB); Peter McCormack, Wirral (GB); Anne Hodgson, Wirral (GB)

(73) Assignee: Phoenix Chemicals Limited, Bromborough, Wirral (GB)

( * ) Notice: Subject to any disclaimer, the term of this patent is extended or adjusted under 35 U.S.C. 154(b) by 421 days.

(21) Appl. No.: 12/438,643

(22) PCT Filed: Aug. 22, 2007

(86) PCT No.: PCT/GB2007/050503
§ 371 (c)(1),
(2), (4) Date: Aug. 10, 2009

(87) PCT Pub. No.: WO2008/023205
PCT Pub. Date: Feb. 28, 2008

(65) Prior Publication Data

US 2010/0016604 A1   Jan. 21, 2010

(30) Foreign Application Priority Data

Aug. 25, 2006   (GB) .................................. 0616865.2

(51) Int. Cl.
*C07D 213/38* (2006.01)
(52) U.S. Cl. ...................................................... 546/262
(58) Field of Classification Search ................... 546/262
See application file for complete search history.

(56) References Cited

U.S. PATENT DOCUMENTS

| | | | |
|---|---|---|---|
| 2,924,604 A | 2/1960 | Steinhards et al. |
| 3,773,775 A | 11/1973 | Hagedorn |
| 5,130,438 A | 7/1992 | Hsiao et al. |
| 2006/0183777 A1 | 8/2006 | Huang et al. |

OTHER PUBLICATIONS

Amin et al., "Synthesis of Carbon-14 Labeled 1-(2-Hydroxylminomethyl)-1-pyridino-3-(4-carbamoyl-1-pyridino)-2-oxapropane Dichloride Monohydrate [14C]HI-6H2O", Journal of Labelled Compounds and Radiopharmaceuticals, vol. 39, No. 11, pp. 875-884, Mar. 17, 1997.

Balan et al., "Synthesis of Tritium Labelled Oximes: 2-pyridine aldoxime methiodide (2-pam) and 1-(2-hydroxyiminomethylpyridinium)-1-(4-carboxyamidopyridinium)dimethylether dichloride (HI-6), with High Specific Activity", Journal of Labelled Compounds and Radiopharmaceuticals, vol. 33, No. 1, pp. 19-32, 1993.

Hagedorn et al., "Betaine quartarer Salze von Pyridin-2- und-4-aldoxim", Arzneim.-Forsch. (Drug Res.) 26, Nr. 5, pp. 753-755, 1976.

Hagedorn et al., "Darstellung und Quaternierung von Pyridinaldoxim-alkylathern", Arzneim.-Forsch. (Drug Res.) 26, Nr. 7, pp. 1273-1275, 1976.

Nicolas et al., "Synthese Radioactive de Sels D'Ammonium Quaternaires D'Hydroxy Imino Methyl-2 Ou-4 Pyridinium Au Moyen De La N-Methyl Formanilide-14C", Journal of Labelled Compounds and Radiopharmaceuticals, vol. 28, No. 12, pp. 1375-1383, 1990.

Yang et al., "Synthesis of Bis-pyridinium Oxime Antidotes Using Bis(methylsulfonoxymethyl) Ether for Organophosphate Nerve Agents", Bull. Korean Chem. Soc., vol. 24, No. 9, pp. 1368-1370, 2003.

Zhou, X. "Synthesis of O-benzoyl Pyridine-2- and 4-Aldoxime Derivatives and Their Quaternizations", Chemical Journal of Chinese Universities, vol. 5, No. 5, pp. 683-685, 1984.

*Primary Examiner* — Patricia Morris
(74) *Attorney, Agent, or Firm* — Knobbe, Martens, Olson & Bear, LLP

(57) ABSTRACT

The invention provides a process for the manufacture of HI 6 dimethanesulfonate comprising contacting an O-protected pyridine aidoxime compound with bis(methylsulphonoxymethyl)ether in a suitable solvent to form an intermediate compound, contacting said intermediate compound with isonicotinamide to form an O-protected HI 6 product precursor, and de-protecting the precursor to form HI 6 dimethanesulfonate.

18 Claims, No Drawings

PROCESS FOR THE MANUFACTURE OF HI-6 DIMETHANESULFONATE

CROSS REFERENCE TO RELATED APPLICATIONS

This application is the national phase under 35 U.S.C. §371 of prior PCT International Application No. PCT/GB2007/050503 which has an International filing date of Aug. 22, 2007, designating the United States of America, which claims the benefit of British Application Number 0616865.2 filed on Aug. 25, 2006, the disclosures of which are hereby expressly incorporated by reference in their entirety and are hereby expressly made a portion of this application.

FIELD OF THE INVENTION

The present invention relates to a process for the manufacture of HI-6, and to certain novel intermediate compounds in the process.

BACKGROUND OF THE INVENTION

HI-6 is a bis-pyridinium oxime antidote to certain organophosphate nerve agents, HI-6 has the chemical formula I:

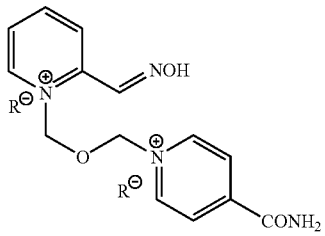

I

Wherein R is a suitable counterion. Suitable counterions include chloride and methanesulphonate.

HI-6 with chloride as the counterion has the chemical name (1-(((4-(aminocarbonyl)pyridinio)methoxy)-methyl)-2-((hydroxyimino)methyl)pyridinium dichloride monohydrate (CAS 34433-31-3), and has been known for many years as a suitable antidote for organophosphate nerve agents. Known regimens for producing HI-6 dichloride (2Cl) have involved the use of bis(chloromethyl)ether as a quaternization reagent for the pyridinium moieties pyridine-2-aldoxime (P2A) and isonicotinamide (INA). The reaction scheme proceeds as follows:

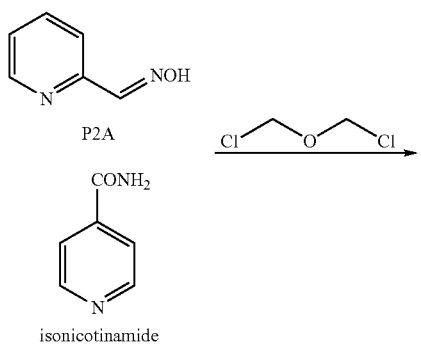

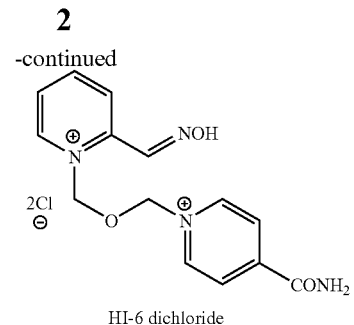

HI-6 dichloride

This conventional method for manufacturing HI-6 has the disadvantage that the reagent bis(chloromethyl)ether is itself highly toxic. A medicament used as antidote against a nerve toxin will preferably be free from highly toxic materials, even incidental amounts thereof left over from a starting reagent. Even if the end product can be guaranteed free of the carcinogenic bis(chloromethyl)ether, it is highly undesirable for this compound even to be used in the manufacturing process because of the potential health hazard to personnel involved in its manufacture and use.

Another recognized HI-6 antidote is HI-6 in which the counterion is methanesulfonate, HI-6 dimethanesulfonate (DMS). Some studies (eg Thiermann et al., International Journal of Pharmaceutics, 137 (1996) 167-176) have reported advantageous properties of HI-6 DMS compared to HI-6 2Cl. HI-6 DMS can be obtained from HI-6 2Cl by an ion exchange chromatography process:

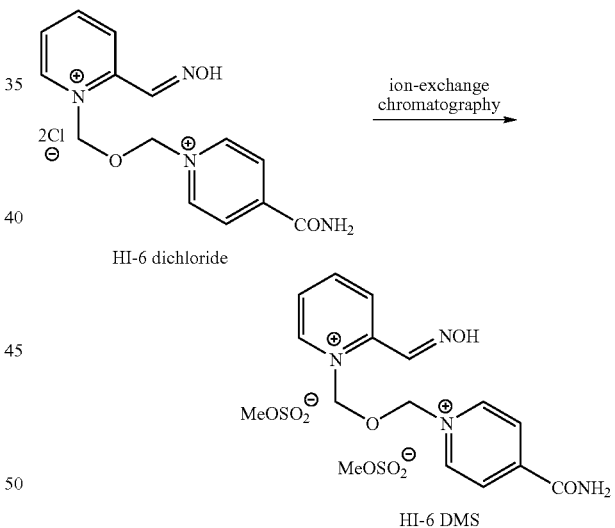

However, this manufacturing route for HI-6 DMS still has the disadvantage that the highly toxic bis(chloromethyl)ether is used in the synthesis, with the attendant risk that traces of this material may be present as a contaminant in any end product medicament comprising HI-6 DMS, or that the reagent used in the manufacturing process may affect adversely the health of any person involved in its manufacture, storage, transport or use.

There have been proposed alternative routes to HI-6 DMS, directly from the starting oxime, and using bis(methylsulfonoxymethyl)ether (BSME) as an alternative quaternization agent. Yang et al. have proposed, in Bull. Korean Chem. Soc. 2003 Vol. 24, No. 9, 1368-1370, such a route but with very poor yields of the product material. Similar problems attend the disclosure of U.S. Pat. No. 5,130,438 of Hsiao et al. In both cases HI-6 DMS yields of 11% (with respect to P2A) are quoted after multiple fractional recrystallization. The scheme for these prior art syntheses may be summarized as:

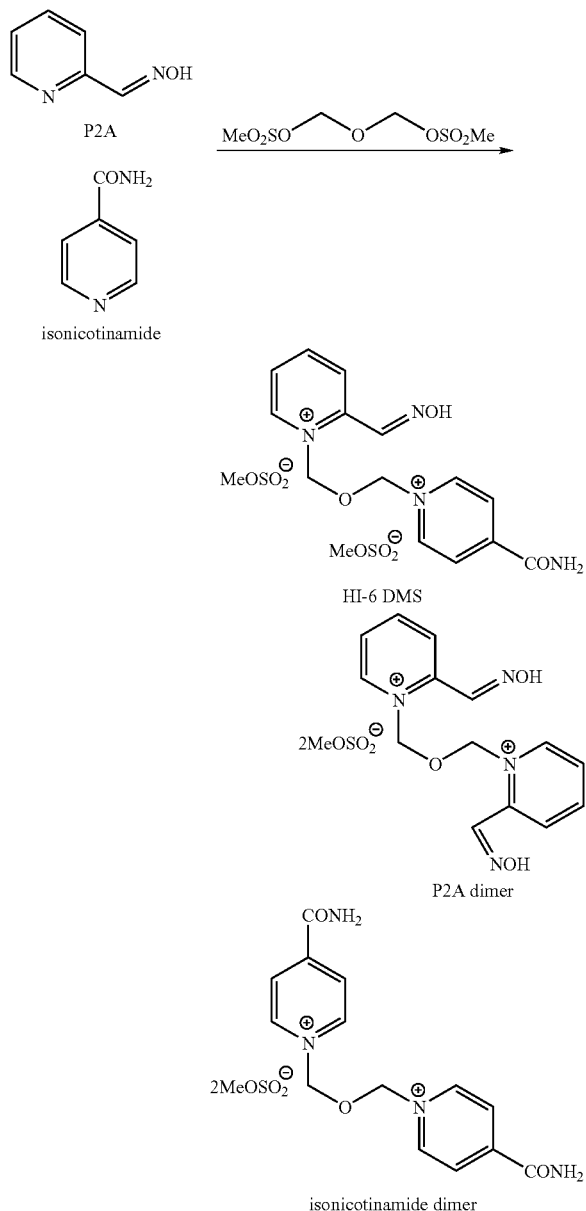

Wherein the pyridine-2-aldoxime and isonicotinamide dimers are unwanted side products, present in the product mixture in unsatisfactorily high proportions. These unwanted side products have similar solubility properties to HI-6 DMS and are difficult to remove from the product. Thus it is difficult to obtain HI-6 DMS of satisfactory purity using such synthetic routes.

SUMMARY OF THE INVENTION

It is an object of the present invention to provide a synthetic route to HI-6 which overcomes or ameliorates some of the aforesaid disadvantages of previous routes. In particular, it is an object of the invention to provide a process for HI-6 production which avoids the use of highly toxic and/or carcinogenic reagents. It is a further object of the invention to provide a convenient industrial scale process for HI-6 manufacture in which product yields and/or purities are commercially satisfactory, and improved with respect to the prior art.

DETAILED DESCRIPTION OF THE PREFERRED EMBODIMENT

According to the present invention there is provided a process for the manufacture of HI-6 R, wherein R is a suitable counterion or counterion pair, comprising contacting an O-protected pyridine aldoxime compound with an (R'-alkyl) ether, wherein R' corresponds to the counterion or one counterion of the pair, in a suitable solvent to form an intermediate compound, contacting said intermediate compound with isonicotinamide to form an O-protected HI-6 product precursor, and de-protecting the precursor to form HI-6 R.

It will be appreciated that the HI-6 cation is divalent and that R in this case necessarily comprises a divalent anion or two univalent anions. Preferably, it will be two univalent anions, each univalent anion corresponding to R' and the (R'-alkyl)ether is in this case being a bis-(R' alkyl)ether. In the case of R being a divalent anion, R will correspond with R' in this case.

The process proceeds via the quaternization of the pyridine aldoxime. Preferably the pyridine aldoxime is a pyridine-2-aldoxime. Therefore the invention provides a process for the manufacture of HI-6 R, (wherein R is a suitable counterion or counterion pair) comprising the quaternization of an O-protected pyridine-2-aldoxime compound with a bis(R'-alkyl) ether, wherein R' corresponds to the counterion or one counterion of the pair, in a suitable solvent to form an intermediate compound, contacting said intermediate compound with isonicotinamide to effect quaternization of the isonicotinamide to form an O-protected HI 6 product precursor, separation of said O-protected HI-6 from unwanted impurities and de-protecting the O-protected HI6 to form HI-6 R.

Preferably, the counterion is methanesulfonate.

Preferably, the alkyl group is a short chain alkyl (alkylene) group, for example $C_{1-4}$. Preferably it is methyl (methylene).

Hagedorn has previously reported quaternization of O-methyl pyridine-2-aldoxime in Arzneimittel Forschung vol 27, 1976, 1273. However, O-alkyl protecting groups are not readily removed. Attempted quaternizations of a number of O-substituted species with more readily removed protecting groups such as O-benzoyl pyridine-2-aldoxime derivatives with methyl iodide has been disclosed previously in the Chemical Journal of Chinese Universities 1984, Vol 5, No. 5, pp 683 by Zhou Xirui. In this work it was found that O-benzoyl pyridine-2-aldoxime derivatives did not form the normal quaternized products rather β-elimination of the aldoxime functional group occurred to give quaternized 2-cyanopyridine derivatives. Thus the desired oxime function was destroyed during the quaternization process.

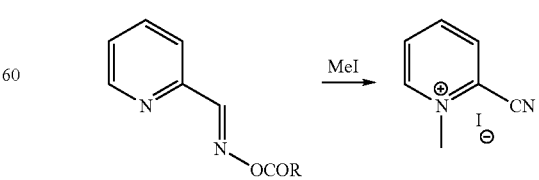

We have prepared a number of O-substituted pyridine-2-aldoximes and we have found that quaternization of these derivatives is possible and that β-elimination does not occur to any significant extent. In fact it has been found that in many instances O-protection greatly facilitates the quaternization reaction to give much higher yields of the desired products than conventional non-protected routes. Additionally and of great benefit, O-protection affords new solubility properties to these intermediate O-protected quaternized species that allows for the convenient removal of impurities and the subsequent enhancement in purities and yields.

Thus, the present invention provides a process for the manufacture of HI 6 DMS comprising contacting an O-protected pyridine aldoxime compound with bis(methylsulfonoxymethyl)ether (BSME) in a suitable solvent to form an intermediate quaternized compound, contacting said intermediate compound with isonicotinamide in a suitable solvent to allow quaternization of isonicotinamide to form an O-protected HI-6 product precursor, separation of unwanted impurities from the O-protected HI-6 product precursor and de-protecting the precursor to form HI-6 DMS.

mixture such that precipitation/crystallization of the unwanted impurities occurs. These are then removed by filtration leaving in the filtrate the O-protected HI-6 product precursor. Suitable solvents for such a process include aqueous alcohols (preferably methanol, ethanol), acetone. Other suitable solvents will be apparent to those skilled in the art.

The protected product precursor may be de-protected for example by contacting the precursor with a de-protecting agent comprising a solvent and/or reagent suitable for removing the protecting group. Suitable de-protecting agents include protic solvents or solvent mixtures containing labile protons, combinations of solvent mixtures containing labile protons and acylation catalysts such as 4-dimethylaminopyridine. Examples of such de-protecting agents are solvents such as ethanol or water or combinations thereof.

One preferred process according to the invention proceeds according to the following scheme:

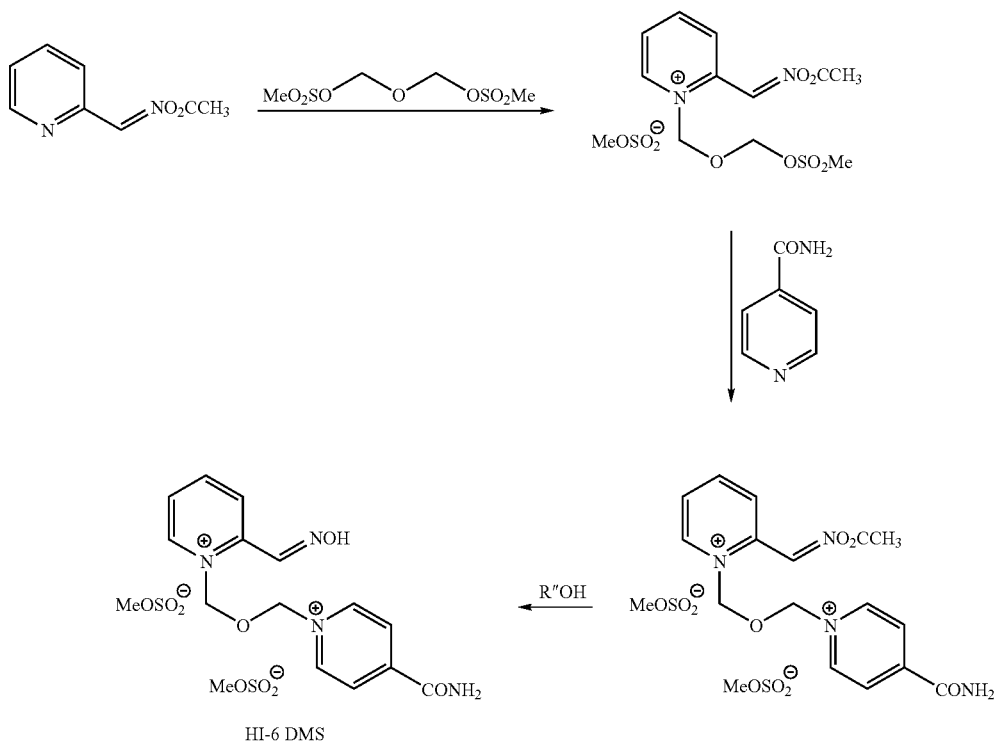

The protecting group is preferably an ester group, more preferably an acetate group.

Suitable solvents for the quaternization of O-protected pyridine aldoxime with BSME include: chlorinated hydrocarbons, acetonitrile, ethers such as tetrahydrofuran, dioxane and dimethoxyethane.

Suitable solvents for the quaternization of isonicotinamide with the O-protected intermediate include dimethylformamide, dimethylacetamide, dimethylsulfoxide, acetonitrile, N-methylpyrrolidinone.

The unwanted isonicotinamide containing impurities are separated from the O-protected HI-6 product precursor by trituration of the reaction mixture with a suitable solvent Wherein R"OH is an alcoholic and/or protic solvent or a mixture of two or more thereof.

Also provided in accordance with the invention is a protected HI-6 product precursor. Preferably the precursor is protected by an ester group.

This route to HI-6 DMS from BSME using protected P2A species offers a number of advantages over the non-protected P2A chemistry. The protected route offers more facile operability for scaled up industrial manufacture. For example in the non-protected chemistry and on lab scale the reaction of P2A with BSME leads to a tar-like paste and a supernatant; this supernatant is decanted off and the paste taken through the process. This decantation step is difficult to achieve on manufacturing scale and such pastes are difficult to stir and mix with further reagents. Advantageously the changed solubility properties imparted by the protecting group mean that no pastes and decantation steps are required during this route. This allows for easier processing.

The protected route allows for greatly enhanced yields of HI-6 DMS. Reported yields of HI-6 DMS from the non-protected routes are in the region of 10% after multiple fractional recrystallisation steps. We have found the non-protected route to be quite irreproducible, with the best results obtained when using elevated mole equivalent amounts of BSME relative to P2A (2-3 mole equivs relative to P2A). In any event yields obtained using non-protected routes were never greater than 10-12%. The protected route will reproducibly give crude HI-6 DMS in 50-60% yield (relative to P2AOAc) of 85-95% purity. This material can be recrystallised to pure HI6 DMS in 70-80% yield leading to an overall yield reproducibly in the range of 35-42% (relative to P2AOAc).

| Direct comparison of yields and purities of crude HI-6DMS derived from protected and non-protected routes | | | |
|---|---|---|---|
| Route | Substrate | Yield of isolated solid (%) wrt to starting P2A species | Purity (area %) |
| Protected | P2AOAc | 55 | 88 |
| Non-Protected | P2A | 43 | 4 |

The invention will now be more particularly described with reference to the following examples.

Synthesis of O-Protected pyridine-2-aldoxime substrates

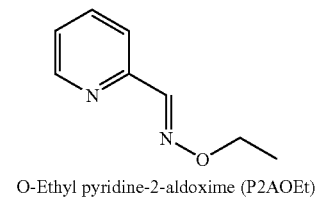

O-Ethyl pyridine-2-aldoxime (P2AOEt)

To sodium hydroxide (33.5 g of a 10% w/w aqueous solution, 83.8 mmol) with overhead stirring was charged solid P2A (10 g, 81.9 mmol) under a blanket of $N_2$. Toluene (144 g), tetrabutylammonium bromide (1.3 g, 4.1 mmol) and ethyl bromide (10.6 g, 97.5 mmol) were added to give two phases. The mixture was heated to 80° C. with good stirring. After 3 hours, sampling and analysis by HPLC revealed that >90% conversion had occurred. The mixture was cooled to 23° C. and the brown organic phase was isolated, dried over anhydrous magnesium sulphate ($MgSO_4$), and filtered. The solvent was removed under reduced pressure (40 mbar) to yield 7.44 g of a brown oil (60.5% yield). Analysis by $^1H$ nmr indicated trace quantities of ethyl bromide, toluene and P2A. This oil was then distilled (81° C., 2 mbar) to give a colourless oil; $^1H$ NMR ($CDCl_3$, 250 MHz): δ 1.35 (t, 3H, J=7.1 Hz), 4.28 (q, 2H, J=7.1); 7.25 (m, 1H); 7.70 (m, 1H); 7.80 (m, 1H); 8.17 (s, 1H), 8.61 (m, 1H)ppm. $^{13}C$ NMR ($CDCl_3$, 63 MHz): δ 14.61, 70.36, 120.99, 123.85, 136.43, 148.89, 149.68, 151.88 ppm.

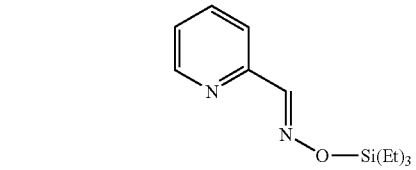

O-Triethylsilyl pyridine-2-aldoxime (P2AOTES)

To a vessel was charged solid P2A (2 g, 16.4 mmol) under a blanket of $N_2$. Anhydrous methylene chloride (MDC, 10.6 g), triethylamine (1.8 g, 17.9 mmol) and 4-dimethylaminopyridine (4-DMAP, 4 mg, 0.3 mmol) were added and the mixture stirred. Triethylsilyl chloride (2.5 g, 16.6 mmol) in MDC (10.6 g) was added dropwise and with good stirring; an exotherm was noted (26 to 31° C.). At the end of the addition a white suspension resulted. The mixture was stirred at 23° C. for 12 hours and then MDC (106 g) was added. The mixture was then washed with ice cold water (3×100 g), the organic phase isolated, dried over $MgSO_4$, filtered and the solvent was removed under reduced pressure to give 3.24 g of a pale yellow oil (83.7% yield); $^1H$ NMR ($CDCl_3$, 250 MHz): δ 0.83 (q, 6H, J=7.1 Hz), 1.06 (t, 2H, J=7.1); 7.25 (m, 1H); 7.68 (m, 1H); 7.88 (m, 1H); 8.31 (s, 1H), 8.59 (m, 1H)ppm. $^{13}C$ NMR ($CDCl_3$, 63 MHz): δ 4.33, 6.64, 120.57, 123.88, 136.34, 149.42, 152.36, 154.23 ppm.

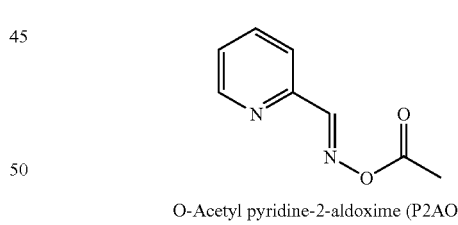

O-Acetyl pyridine-2-aldoxime (P2AOAc)

A 14% w/w solution of acetic anhydride (1 moleq) in MDC was slowly charged to a 14% w/w solution of P2A (10 g, 81.9 mmol), triethylamine (8.27 g, 81.9 mmol) and catalytic 4-DMAP (0.004 g) in MDC at room temperature under $N_2$. After stirring the reaction mixture for 14 hours the mixture was quenched into ice water (150 g), the organic phase was washed with ice water (150 g), dried ($MgSO_4$), filtered and the solvent removed under reduced pressure to afford 12.2 g (91% yield) of a pale yellow transparent oil, which crystallised to a white solid on standing; $^1H$ NMR ($CDCl_3$, 250 MHz) δ 2.2 (s, 3H), 7.3 (m, 1H), 7.8 (t, 1H), 8.0 (d, 1H), 8.4 (s, 1H), 8.7 (d, 1H)ppm. $^{13}C$ NMR ($CDCl_3$, 63 MHz): δ 19.54 ($OC(O)CH_3$), 122.00, 125.51, 136.70, 149.87, 149.93, 156.57, 168.31 ppm.

Quaternization Reactions
Reaction of O-Ethyl pyridine-2-aldoxime (P2AOEt) with BSME and isonicotinamide

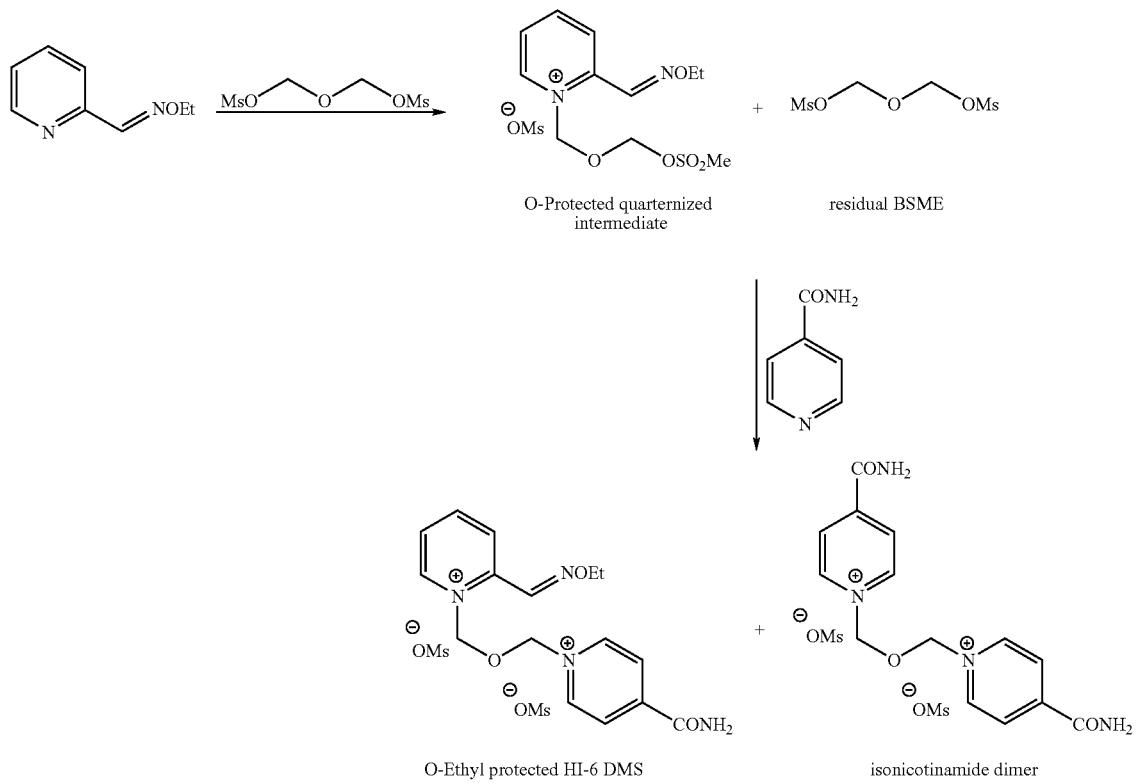

O-Protected quaternized intermediate residual BSME

O-Ethyl protected HI-6 DMS isonicotinamide dimer

Solid BSME (1.4 g, 5.9 mmol) was placed in a vessel under a slow stream of $N_2$. Acetonitrile (2.1 g) was added and the resulting mixture stirred. P2AOEt (0.9 g, 5.9 mmol) in acetonitrile (4.8 g) was added at 23° C. and the resulting mixture stirred for 22 hours. Solid isonicotinamide (0.69 g, 5.6 mmol) was added and the mixture stirred for 5 hours and then held at −20° C. for 4 days, The resulting heterogeneous slurry was warmed to 23° C. and then filtered. The filter cake/paste was then stirred in ethanol (15.8 g) for 1 hour and filtered to give a dry solid. HPLC and $^1H$ nmr analysis indicated it to be the dimethanesulfonate salt of isonicotinamide dimer. The filtrates were combined and the solvent was removed under reduced pressure to give a brown oil that crystallized on standing to yield 1.4 g of solid. $^1H$ NMR ($d_6$-DMSO, 250 MHz): δ 1.30 (t, 3H, OCH$_2$CH$_3$), 2.34 (s, 6H, OSO$_2$CH$_3$), 4.40 (q, 2H, OCH$_2$CH$_3$); 6.24 (s, 2H, CH$_2$OCH$_2$), 6.39 (s, 2H, CH$_2$OCH$_2$), 7.25 (m, 1H); 7.70 (m, 1H); 7.80 (m, 1H); 8.23 (m, 1H), 8.32 (s, 1H, NH), 8.52 (m, 3H), 8.75 (m, 3H, 2×CH, 1×NH), 9.25 (m, 1H), 9.36 (m, 2H) ppm.

Reaction of O-Triethylsilyl pyridine-2-aldoxime (P2AOTES) with benzyl bromide

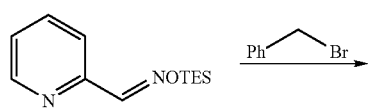

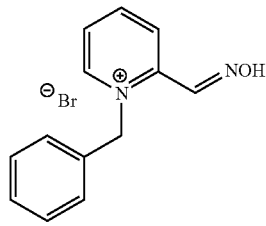

To a solution of P2AOTES (0.12 g, 0.50 mmol) in MDC, acetonitrile (4 g/3.5 g) was added benzyl bromide (0.17 g, 1.0 mmol, 2.0 moleq.). The mixture was refluxed for 2 days to give a heterogeneous slurry. The mixture was filtered and the cake was rinsed with acetonitrile (2.5 g) and dried using air-flow. Analysis of the cake by HPLC indicated >98% (area) purity. $^1H$ NMR (D$_2$O, 250 MHz): δ 5.88 (s, 2H, CH$_2$Ph), 7.14 (m, 2H), 7.34 (m, 3H); 7.95 (m, 1H), 8.27 (m, 1H), 8.46 (m, 1H); 8.5 (s, 1H); 8.80 (m, 1H)ppm. $^{13}C$ NMR (D$_2$O, 63 MHz): δ 61.64 (CH$_2$Ph), 127.16, 127.45, 128.00, 129.41, 129.46, 132.43, 141.99, 145.94, 146.00, 147.14 ppm.

Example 1

Preparation of HI-6 DMS

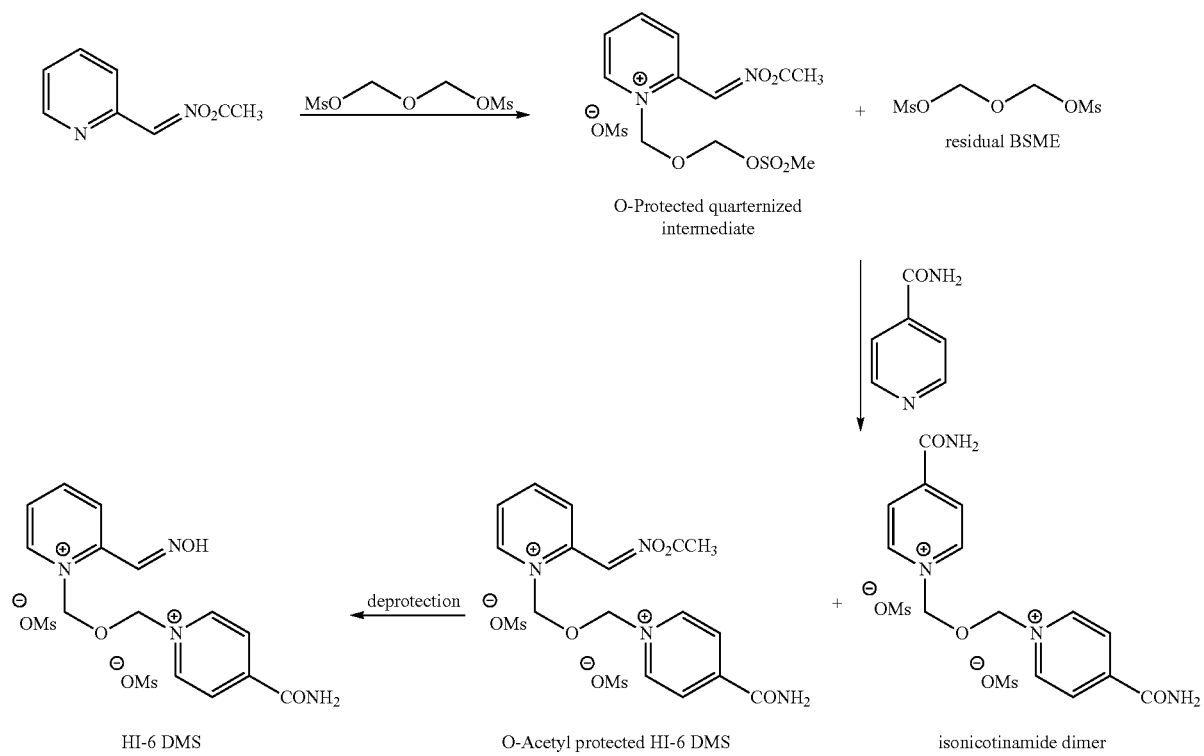

To a solution of BSME (2.89 g) and acetonitrile (11.3 g) was slowly added a solution of P2A (2.03 g) in chilled (−20° C.) tetrahydrofuran (71.2 g) over 30 minutes under nitrogen. The solvent was partially evaporated over 2 hours and acetonitrile (11.3 g) and tetrahydrofuran (71.2 g) was added to form a gum. The supernatant liquid was decanted and acetonitrile (14 ml) added to the gum. Isonicotinamide (1.2 g) was added and the mixture stirred at room temperature for 20 hours. The solvent was removed under reduced pressure and the residue triturated with ethanol (49.5 g). The slurry was filtered to remove isonicotinamide dimer. The filtrate was stirred overnight. The solid was collected by filtration and the cake washed with ethanol to yield HI-6 DMS (1.9 g, 90% area by HPLC, 29% th. yield).

Example 2

Preparation of HI-6 DMS

To a solution of BSME (2.89 g) and acetonitrile (11.3 g) was slowly added a solution of P2A (2.03 g) in acetonitrile (17.8 g) over 1.5 hours under nitrogen and the mixture stirred for 20 hours. Isonicotinamide (1.2 g) and acetonitrile (3.95 g) was added and the mixture stirred at room temperature for 20 hours. The solvent was removed under reduced pressure and the residue triturated with ethanol (49.5 g). The slurry was filtered to remove 'isonicotinamide dimer'. The homogeneous filtrate was stirred overnight. The solid was collected by filtration and the cake washed with ethanol to yield HI 6 DMS (2 g, 85% area by HPLC, 30% th. yield). The crude HI-6 DMS was recrystallised form aqueous ethanol to give 1.2 g HI-6 DMS (>98% area by HPLC). This is a 21% overall yield from P2AOAc.

Example 3

Preparation of HI-6 DMS

Solid BSME (20 g, 84.0 mmol, 1.2 moleq.) was charged to a dry vessel under $N_2$ and a solution of P2AOAc (11.6 g, 70.0 mmol, 1.0 moleq) in MDC/acetonitrile (85.3 g/9.2 g) was added. The mixture was stirred for 6 hours and then isonicotinamide (11.4 g, 93.3 mmol) in dimethylformamide (25.8 g) was added. The mixture was stirred out for 17 hours. Ethanol (370 g) was added and the mixture was stirred for ca 6 hours. The resulting slurry was filtered. The homogeneous filtrate was then placed in a vessel and stirred until deprotection was complete. The resulting slurry was then filtered to give 17.8 g (53% yield based on P2AOAc) of an off-white powder (HPLC 95% by area). 5 g of this cake was then re-crystallized from aqueous ethanol (44.4 g) to give 3.9 g of a white solid, HPLC (>99% by area); $^1$H NMR ($D_2O$, 250 MHz): δ 2.67 (s, 6H), 6.22 (s, 2H); 6.34 (s, 2H); 8.03 (m, 1H); 8.42 (m, 3H); 8.60 (m, 2H), 8.98 (d, 1H); 9.14 (d, 2H)ppm. $^{13}$C NMR ($D_2O$, 63 MHz): δ 38.48 ($OS(O)_2CH_3$), 85.58, 86.86, 126.70, 127.57, 127.95, 141.89, 144.54, 145.17, 146.97, 148.18, 150.79, 166.26 ($C(O)NH_2$)ppm. Found: C, 40.24; H, 4.59; N. 11.68. Calculated for $C_{16}H_{22}N_4O_9S_2$; C, 40.16; H, 4.63; N, 11.71.

What is claimed is:

1. A process for the manufacture of HI-6 R, wherein R is a suitable counterion or counterion pair, comprising contacting an O-protected pyridine aldoxime compound with an (R'-alkyl)ether, wherein R' corresponds to the counterion or one counterion of the pair, in a suitable solvent to form an intermediate compound, contacting said intermediate compound with isonicotinamide to form an O-protected HI-6 product precursor, and de-protecting the precursor to form HI-6 R.

2. A process according to claim 1 wherein R comprises two univalent anions, each univalent anion corresponding to R', and the (R'-alkyl)ether is a bis(R'-alkyl)ether.

3. A process according to claim 1 wherein the O-protected pyridine aldoxime compound has a formula:

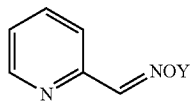

wherein Y is a protecting group.

4. A process according to claim 3 wherein the protecting group comprises an ester group.

5. A process according to claim 4 wherein the protecting group comprises an acetate group.

6. A process according claim 1 wherein the alkyl group is selected from the group consisting of a short chain alkyl group and a short chain alkylene group.

7. A process according to claim 6 wherein the alkyl group is selected from the group consisting of a $C_{1-4}$ alkyl group and a $C_{1-4}$ alkylene group.

8. A process according to claim 7 wherein the alkyl group is selected from the group consisting of methyl and methylene.

9. A process according to claim 1 wherein R' is methanesulphonate.

10. A process according to claim 9 wherein the O-protected pyridine aldoxime compound is bis(methylsulphonoxymethyl)ether and wherein HI-6 R is HI-6 dimethanesulfonate.

11. A process according to claim 1 further comprising a step of contacting a reaction mixture containing the O-protected HI-6 product precursor and impurities with a solvent effective for dissolving the O-protected HI-6 product precursor, precipitating the impurities and removing the impurities by filtration.

12. A process according to claim 11 wherein the impurities comprise isonicotinamide dimer.

13. A process according to claim 1 wherein the O-protected HI-6 product precursor is de-protected by contacting with a de-protecting agent.

14. A process according to claim 13 wherein the de-protecting agent comprises at least one member of the group consisting of a solvent that removes the protecting group and a reagent that removes the protecting group.

15. A process according to claim 13 wherein the O-protected HI-6 product precursor is triturated with the de-protecting agent to effect the de-protection.

16. A process according to claim 13 wherein the de-protecting agent comprises at least one member of the group consisting of an alcoholic solvent a protic solvent.

17. A process according to claim 16 wherein the solvent comprises at least one member of the group consisting of ethanol and water.

18. A process according to claim 1 which proceeds according to the following scheme:

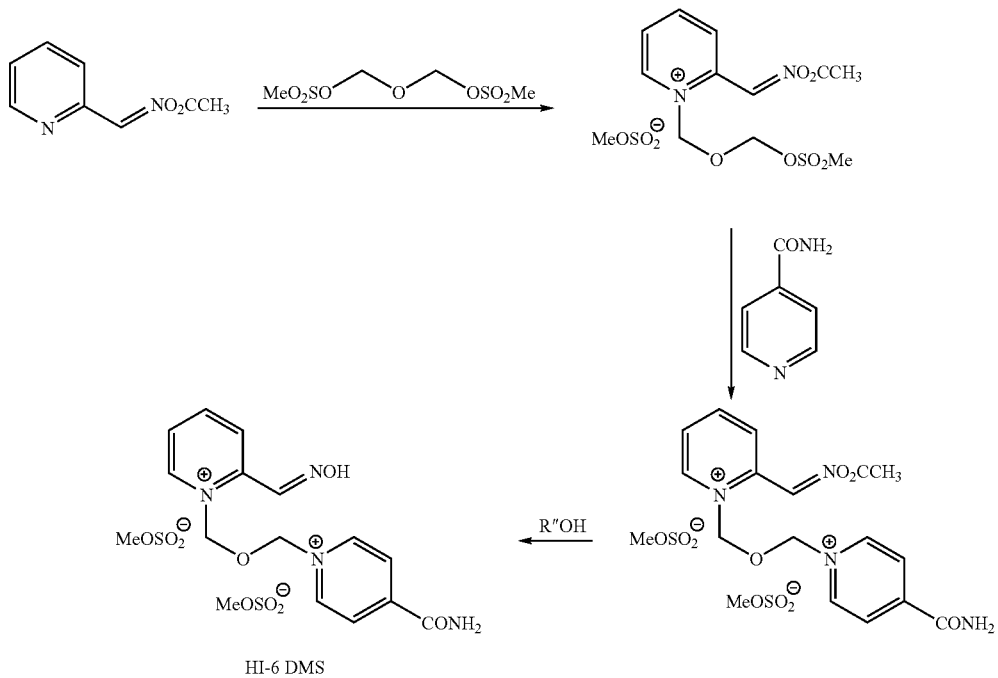

wherein R"OH is selected from the group consisting of at least one an alcoholic solvent, at least one protic solvent, and mixtures thereof.

* * * * *

UNITED STATES PATENT AND TRADEMARK OFFICE
CERTIFICATE OF CORRECTION

PATENT NO. : 8,143,406 B2
APPLICATION NO. : 12/438643
DATED : March 27, 2012
INVENTOR(S) : Jonathan Eddolls et al.

It is certified that error appears in the above-identified patent and that said Letters Patent is hereby corrected as shown below:

Title Page 1 (Item 56) Col 2, Line 2, Under Other Publications, change ""Hydroxylminomethyl)" to --Hydroxylaminomethyl)--.

Title Page 1 (Item 57) Abstract, Line 3, Change "aidoxime" to --aldoxime--.

At Column 1, Line 26 (Approx.), Change "agents," to --agents.--.

At Column 9, Line 43 (Approx.), Change "days," to --days.--.

At Column 10, Line 56 (Approx.), Change "MDC," to --MDC/--.

At Column 13, Line 21 (Approx.), In Claim 6, change "according" to --according to--.

Signed and Sealed this
Twenty-fourth Day of July, 2012

David J. Kappos
*Director of the United States Patent and Trademark Office*